United States Patent
Genosar et al.

(10) Patent No.: US 7,918,843 B2
(45) Date of Patent: Apr. 5, 2011

(54) CONTROLLABLE DRUG DELIVERY DEVICE

(75) Inventors: Amir Genosar, Boulder, CO (US);
Jonathan Goldstein, Jerusalem (IL);
Niles A. Fleisher, Rehovot (IL); Yehuda Bachar, Givat Shmuel (IL); Yossi Aldar, Tel-Aviv (IL)

(73) Assignee: Steadymed Ltd., Tel-Aviv (IL)

( * ) Notice: Subject to any disclaimer, the term of this patent is extended or adjusted under 35 U.S.C. 154(b) by 0 days.

(21) Appl. No.: 12/604,278

(22) Filed: Oct. 22, 2009

(65) Prior Publication Data

US 2010/0087778 A1 Apr. 8, 2010

Related U.S. Application Data

(63) Continuation of application No. PCT/IL2008/000549, filed on Apr. 27, 2008.

(60) Provisional application No. 60/925,651, filed on Apr. 23, 2007.

(51) Int. Cl.
*A61K 9/22* (2006.01)
*A61M 31/00* (2006.01)

(52) U.S. Cl. ...................... 604/890.1; 604/67

(58) Field of Classification Search .............. 320/150, 320/132; 324/426–436
See application file for complete search history.

(56) References Cited

U.S. PATENT DOCUMENTS

| 6,122,488 A * | 9/2000 | Leizerovich et al. ........... 455/78 |
| 6,485,465 B2 * | 11/2002 | Moberg et al. ................ 604/154 |
| 6,577,039 B2 | 6/2003 | Ishida et al. |
| 2003/0136189 A1 | 7/2003 | Lauman et al. |
| 2004/0068224 A1 * | 4/2004 | Couvillon et al. .............. 604/67 |
| 2006/0102455 A1 | 5/2006 | Chiang et al. |
| 2007/0062250 A1 | 3/2007 | Krulevitch et al. |

FOREIGN PATENT DOCUMENTS

| WO | WO01/89607 A2 | 11/2001 |
| WO | WO2007/010522 A1 | 1/2007 |
| WO | WO 2007010522 A1 * | 1/2007 |
| WO | WO2007/129317 A1 | 11/2007 |

* cited by examiner

*Primary Examiner* — Nicholas D Lucchesi
*Assistant Examiner* — Jenna Zhang
(74) *Attorney, Agent, or Firm* — McCarter & English, LLP (57) ABSTRACT

A controllable drug delivery device for delivering a liquid injectable drug, the device comprising a drug reservoir (22), a drug administration device (28), a displacement-generating battery (20), and a current-depletion circuit (85), wherein displacement generated by the battery as current is depleted from the battery by the current depletion circuit displaces a wall of the drug reservoir thereby causing the reservoir to expel liquid injectable drug contained therein via the drug administration device, and wherein the drug delivery device further includes a controller (78) that is responsive to a measured parameter indicative of displacement generated by the battery for applying a variable load (80) across the battery in order to provide a substantially constant-current depletion of the battery and thereby cause the drug delivery device to deliver a substantially constant drug delivery rate.

19 Claims, 8 Drawing Sheets

CONTROLLABLE DRUG DELIVERY DEVICE

This application is a continuation of International Application No. PCT/IL2008/000549, filed Apr. 27, 2008, which designates the United States, and claims priority to U.S. Provisional Application No. 60/925,651, filed Apr. 23, 2007, all of which are incorporated by reference in their entireties as if fully set forth herein.

FIELD OF THE INVENTION

The present invention is in the field of drug-delivery devices. In particular, this invention describes the use of a controllable drug delivery device driven by a displacement-generating battery.

BACKGROUND OF THE INVENTION

Drug delivery devices such as infusion pumps typically require high standards of controllability in order to ensure that the drug delivery is reliable and accurate. WO 2007/129317 by some of the present inventors teaches the use of a displacement-generating battery to drive a miniature drug delivery device. However, this application does not teach the control elements of such a device required to ensure accuracy and reliability. Intercalation is a known process whereby intercalating species within a battery cell penetrate an electrode and arrange themselves therein. The intercalating species can include an ion, a proton, an alkali metal or an alkaline earth metal. The electrode may undergo expansion or contraction upon intercalation. For example, the intercalating species may be a Lithion ion, and the electrode whose volume is changed may contain tin (Sn) or silicon (Si). In these examples and others, the volume change of the electrode can cause the battery cell to serve as an actuator capable of applying motion to a physical object connected to the actuator. The major expansion that can be provided by using a Lithium-Tin intercalation reaction is known in the prior art. For example, the University of South Carolina Research has been reported a volume expansion of 259%. Prior art describing the use of intercalation to perform actuation includes U.S. Pat. No. 6,577,039, US 20060102455 as well as references cited by these patents.

WO 2007/010522 in the name of the present applicant teaches a drug delivery device that utilizes the volume expansion to implement a slow-infusion drug-delivery device.

WO 2007/129317 also in the name of the present applicant and published Nov. 15, 2007 (i.e. after the priority of the present application) likewise teaches a drug delivery device that utilizes the volume expansion to implement a slow-infusion drug-delivery device US 2007/0062250 describes a servo-type control mechanism for an electronically controlled infusion pump where a (magnetic) position sensor is the source of positional feedback for the controller of the pump. The actual position, as determined solely by this sensor, is compared to the desired or expected position, and the pump powered accordingly in order to close any gap between the actual and the theoretical.

SUMMARY OF THE INVENTION

Therefore, an object of the present invention is to provide a control system for a miniature drug-delivery based on a displacement-generating battery and that incorporates actual positional information provided by a displacement sensor to obtain two indications of volumetric drug delivery—one based on battery cell depletion and one based on measured displacement. An algorithm combining both indications can serve to provide more accurate data concerning the actual drug delivery than either one alone. Additionally, by comparing these two indications, device malfunctions can be detected and the controller can then act according to the program for such conditions, thereby adding a further safety feature to the device.

The present invention provides a low-profile, patch-like, drug-delivery device, capable of providing controlled slow infusion of drugs into humans. The device comprises at least one battery cell and at least one drug reservoir, where a displacement of at least one wall of the battery cell directly or indirectly causes displacement of at least one displaceable or flexible wall in said drug reservoir, thereby driving the drug infusion. The drug-delivery device further comprises means for determining the displacement achieved and a drug administration means such as a cannula and a cannula insertion device, the latter being configured to optimize the low profile of the device as a whole. The cannula insertion mechanism may be at least partially mounted in parallel with the battery. In some embodiments, the battery cell is based on the phenomenon of expansion/contraction due to intercalation of ion, a proton, an alkali metal or an alkaline earth metal into an electrode such as one containing tin or silicon or their compounds. The battery cell may be configured to create displacement directly or via internal hydraulic amplification. In some embodiments, the displacement is produced by discharging the cell in a controlled manner. In some embodiments, a feedback control mechanism is provided to ascertain the extent of the displacement produced and thus the volume of the drug delivered. The invention further incorporates a number of techniques to optimize the expansion of the battery cell, as detailed in the embodiments described below.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

The drug-delivery device of the present invention is presented below in the context of a number of embodiments; it being understood that the present invention may incorporate different combinations of the presented elements.

Figure 1A:
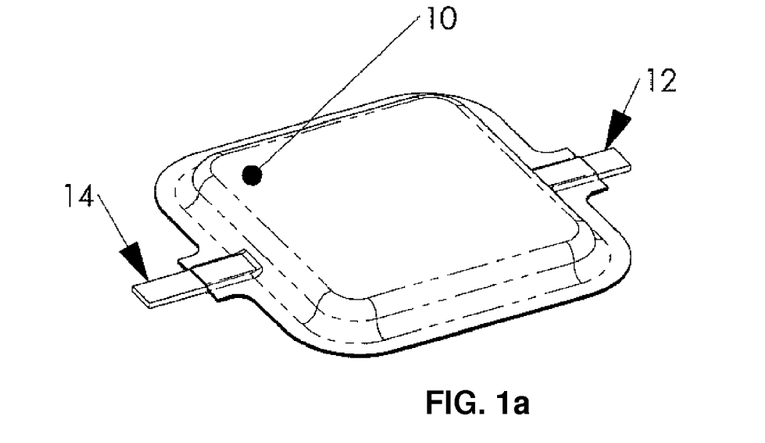
FIGS. 1a to 1d are isometric and cross-sectional views of an embodiment of a thin-film battery cell according to the present invention.
Figure 1B:
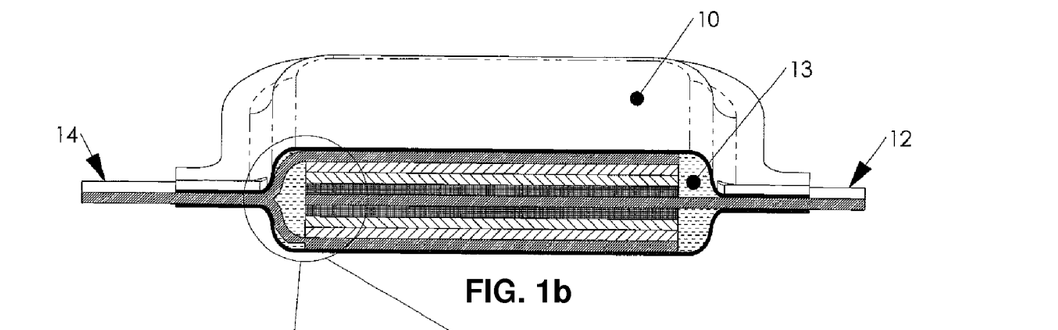

FIGS. 1a and 1b show perspective and cross-sections views showing an embodiment of a multi-layer film configuration of a pouch-type battery comprising a flexible foil package 10 which encloses a multiplicity of cathode-anode layer pairs and an electrolyte 13. Electrical tabs 12 and 14 enter the flexible foil package 10 and are interlaced between the electrode pairs. In this figure, a simple configuration is shown in which the connector 14 to the cathodes is split on entry to the package into a contact layer to the cathodes of the outer layer, while the connector 12 to the anodes enters the middle of the package. This is a simple configuration in which there are only two cathode-anode pairs, connected in parallel. In a more sophisticated configuration, a large number of pairs, preferably in the range of 10 to 50, are connected in the same way, thereby increasing the maximum rate of discharge that can be achieved, and optimizing the stroke achieved. Typical materials used for the flexible foil package 10 of thin-film batteries of this type are PE/Al/PE multi-layer films; but any combination of thin-film plastic materials and/or metalized layers may be used.

Figures 1C, 1D:
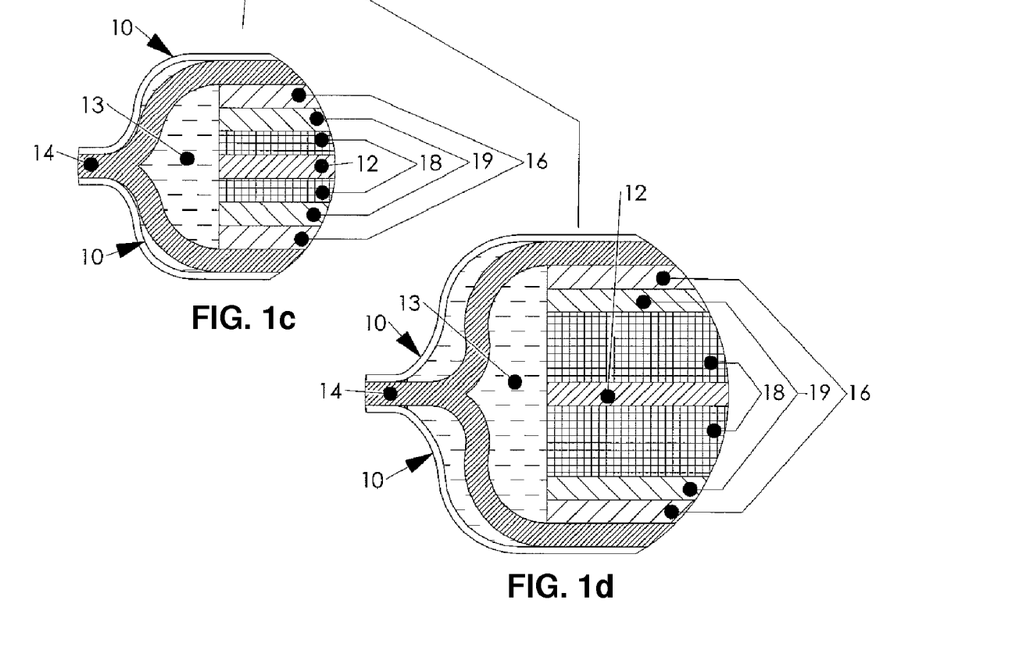

Referring now to FIG. 1c, the marked section of the isometric cut-away view provided in FIG. 1b is shown in a magnified cross-section, in order to explain the principle of operation of the expanding thin-film battery. In this embodiment the cathode connector 14 layer provides the electrical connection to a grid or mesh type cathode 16, the cathode being impregnated with lithium (Li) or similar substance. On the other side of the grid cathode 16 layer, a separator layer 19 is provided and beyond the separator 19, a tin (Sn) anode layer 18 is provided. The other side of the anode 18 is, in turn, in contact with the anode connector layer 12. In this simple model, as there are only two anode-cathode pairs, only one anode connector layer is required. In a configuration with more such pairs, the connectors can be interlaced between each anode-separator-cathode combination. This arrangement can be used to enable simultaneous depletion in parallel of all the anode-cathode pairs. In an alternative embodiment, the connectors can be configured such that the battery cell is divided into subsets of anode cathode couples of pairs, these subsets being connected either in parallel or in series. If desired, as the Li—Sn arrangement produces only 0.4V, a number of such subsets can be connected in series so as to produce a voltage level sufficient to drive the electronics control module (to be described below with reference to FIGS. 7, 8a and 8b), thereby obviating the need for the module to incorporate its own power source or require use of a voltage converter. The separator 19 is typically a porous polymeric material such as polypropylene which enables ion transfer from the cathode grid to the anode. The specific battery chemistry implemented in the preferred embodiment shown here is an intercalation reaction between the lithium ions and the tin layer. More specifically, the lithium ions migrate from grid 16 such as a nickel grid, across the separator 19, and migrate into the tin layer 18. As detailed in WO2007129317, hereby incorporated by reference, this ion migration causes the tin layer 18 to expand greatly.

The use of a grid, matrix or other framework that can house the intercalating species is an important feature of the present invention. This framework is defined as any matrix that can house the intercalating species such that even though the intercalating species is depleted from this matrix, this layer essentially maintains its thickness. Although the theoretical maximum expansion of a tin layer after this intercalation is 259%, if the thickness of the lithium layer were to decline to zero as the lithium is consumed, the net effect (i.e. the expansion of the tin layer minus the disappearance of the lithium layer) would be a reduction in the thickness of the battery cell as a whole by 18%. The use of a fixed grid 16 to "house" the lithium provides the advantage of enabling this layer 16 to largely maintain its previous thickness while the lithium migrates out, its place at least partially being taken by the electrolyte. This is illustrated by FIG. 1d showing the change in thickness of the battery resulting from the expansion of the tin layers 18 as the battery is discharged.

In some embodiments, the battery cell is constructed using superimposed prefabricated layer sandwiches, as per the following example:

Example Battery Layer Sandwich

| | Material | Height | Details |
|---|---|---|---|
| 1 | Li | 100 micron | Embedded in Nickel mesh, 90% open |
| 2 | Separator | 20 micron | Saturated with electrolyte |
| 3 | Sn | 40 micron | Plating the copper current collector from one side |
| 4 | Copper | 30 micron | Current collector |
| 5 | Sn | 40 micron | Plating the copper current collector from the other side |
| 6 | Separator | 20 micron | Saturated with electrolyte |
| 7 | Li | 100 micron | Embedded in Nickel mesh, 90% open |

In this example, the sandwich includes two Sn-Separator-Li arrangements in a 350 micron package. Assembling 20 such sandwiches, one on top of the other, serves to fabricate a 7 mm battery cell. Given that the total thickness of all the Sn layers in this battery cell is 1.6 mm, a 200% expansion of these layers, while the nickel grid layer maintains its initial thickness, will produce an expansion of 3.2 mm, which is 45% of the initial height. Further optimization can be achieved by changing the relative thicknesses of the Li and Sn layers and using a different Sn expansion coefficient in order to maximize the overall expansion achieved and minimize the battery size. For example, by using less lithium and an 80 micron Sn layer which expands by 150% thickness, a 5 mm (starting height) battery can designed, which achieves a 2.8 mm expansion, which is 56% of the original height. In this example, the lithium is from LithChem International, Inc. (Anaheim, Calif., USA), the nickel mesh is MN62 from Precision Forming, (Cortland, N.Y., USA), the electrolyte is LiBF4+GBL (Celgard 3402, from Celgard, LLC, Norderstedt, Germany), the tin powder (Cat #520373) is from Sigma-Aldrich, (St. Louis, Mo., USA), and the copper current collector is Alloy 110 Copper Cat #9709K53, from McMaster (N.Y., USA). The lithium layer is prepared by pressing the lithium into the 90% open nickel mesh until a flat solid layer of 50 microns results. The layers are mounted in the order shown, care being taken that the tabs from each anode layer are all connected together in parallel, and that the tabs from each cathode layer are all connected in parallel. In other embodiments at least some of the layers or features of battery construction are fabricated directly on top of former features or layers of the construction by methods known in the art such as selective deposition.

Advantageously, as opposed to standard infusion pumps, the use of a displacement generating battery is capable of generating very high pressures. As back-pressures within the body are typically of the order of less than 1 atmosphere, standard infusion pumps are generally not designed to generate very high pressures, typically not greater than 5 atmospheres. Accordingly, an infusion pump based on a displacement-generating battery is capable of infusing viscous drugs that standard infusion pumps cannot infuse. In particular, experimental results have shown that the drug-delivery device of the present invention is capable of generating pressures in excess of 20 atmospheres. Furthermore, these results have further demonstrated that highly viscous drugs, in the 20-200 centipoise (cP) range, can be delivered by the drug delivery device of the present invention. Most liquid drugs intended for infusion have a viscosity similar to that of water—where water has a viscosity of only 0.890 cP at room temperature—and typical infusion pumps are designed for this range of viscosities. Thus the capability of the drug-delivery device of the present invention to deliver drugs in the 20-200 cP range is well in excess of the known capability of existing miniature infusion pumps. It has been discovered that many biological drugs such as therapeutic antibodies have higher bioavailability when delivered at high concentrations. At these concentrations, the viscosity increases to the 20-200 cP range, and thus this ability of the drug-delivery device of the present invention to deliver such drugs is highly advantageous.

As opposed to prior art approaches where electrical power needs to be applied to the battery in order to make it expand, the combination of the above battery chemistry (or that where silicon replaces the tin), together with the above grid approach, enables the expansion of the battery cell as it is depleted. Advantageously, this provides for considerable savings in weight, cost, complexity and size relative to a design in which an additional power supply is required.

Figure 2A:
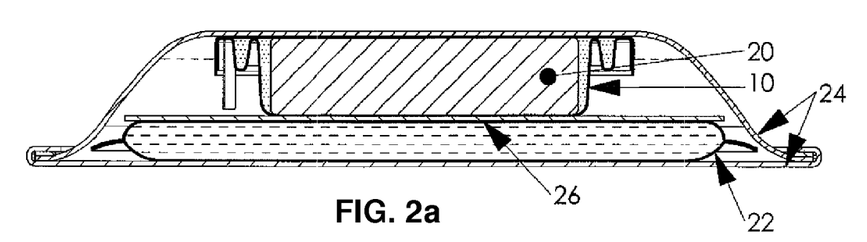
FIGS. 2a to 2c show cross-sectional views of an embodiment of a drug-delivery device of the present invention using the thin-film battery cell shown in FIG. 1.
Figure 2B:
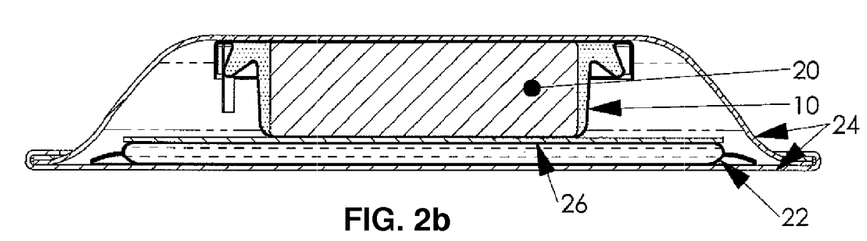
Figure 2C:
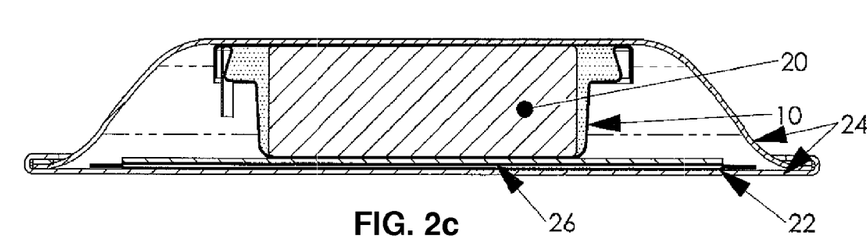

FIGS. 2a to 2c show cross-sectional views of an embodiment of the drug-delivery device of the present invention, which integrates the thin-film battery cell shown in FIG. 1 with a flexible pouch that serves as a drug reservoir 22 for containing a liquid injectable drug. For simplicity of presentation, the battery cell 20 is shown as an integral unit (without showing its internal structure) confined in a pouch 10, and the result of the progressive expansion of this battery cell is shown in FIGS. 2b through 2c. Although this invention in its broadest sense allows for the use of any kind of drug reservoir providing only that it has at least one displaceable wall, the embodiment shown in FIGS. 2a to 2c presents the use of a flexible pouch 22. In a pre-filled version of the drug-delivery device of the present invention, the pouch may be filled with a drug, either prior to insertion into the housing 24 or thereafter. In some embodiments the reservoir pouch is made from a soft film such as soft PVC or PE which may not provide structural strength. In this case a pressure check valve may be desired in an outlet port of the pouch to avoid drug spillage. In other embodiments the reservoir pouch is made from relatively rigid films which provide structural strength and can be designed such that the pouch opposes the battery squeezing action. Appropriate materials for this stiff pouch configuration include rigid PVC or PET.

In the embodiment shown, as the battery cell 20 expands, it displaces a displaceable interfacing plate 26 which serves as the interface between the battery cell 20 and the flexible pouch of the drug reservoir 22. Although theoretically the battery cell 20 could press directly against the flexible pouch, in practice there are a number of reasons to use such a displaceable interfacing plate 26: (1) a smoothing of the displacement effect is achieved; (2) a hermetically sealed boundary between the drug and the battery may be achieved by having this plate connected around its periphery by a flexible means to the housing 24, such that there can be no leakage of battery cell contents into the drug, even if both the drug reservoir and the battery cell are breached, (3) provide a structural element for the mostly "flimsy" pouch and a well-defined anchor to position with other elements of the device, and (4) the displaceable wall is a convenient platform for implementing various flow control devices, fittings and feedback mechanisms as is described below. In some embodiments electronics components and circuitry are implemented in or mounted on top of the interfacing plate 26. In some embodiments the interfacing place 26 is a printed circuit board.

While the expanding battery cell 20 and the drug reservoir pouch 22 constitute the core of the drug-delivery device, a number of additional elements are required to complete the device. These elements may include a drug administration device such as a cannula and its insertion mechanism, a passage to the drug administration device, a one-way valve and a control mechanism. In some embodiments a pressure sensor monitors the pressure in the reservoir or the flow passage for the purpose of early occlusion detection, and/or to support the pump's control and safety systems. Suitable pressure sensors are force sensing resistors provided by Sytek Enterprises, Inc. of British Columbia, Canada.

In some embodiments a resilient biasing device is implemented to counter the expansion action of the battery cell 20 forcing the cell 20 to operate under higher forces, thus reducing the effect of mechanical noises, as well as eliminating backlash. In some embodiments the biasing device is implemented between the battery cell 20 and the reservoir 22. In this way it can also provide a base pressure to the reservoir. In some embodiments the biasing device is implemented in the reservoir 22 or is provided by the reservoir walls.

Figures 3A, 3B, 3C:
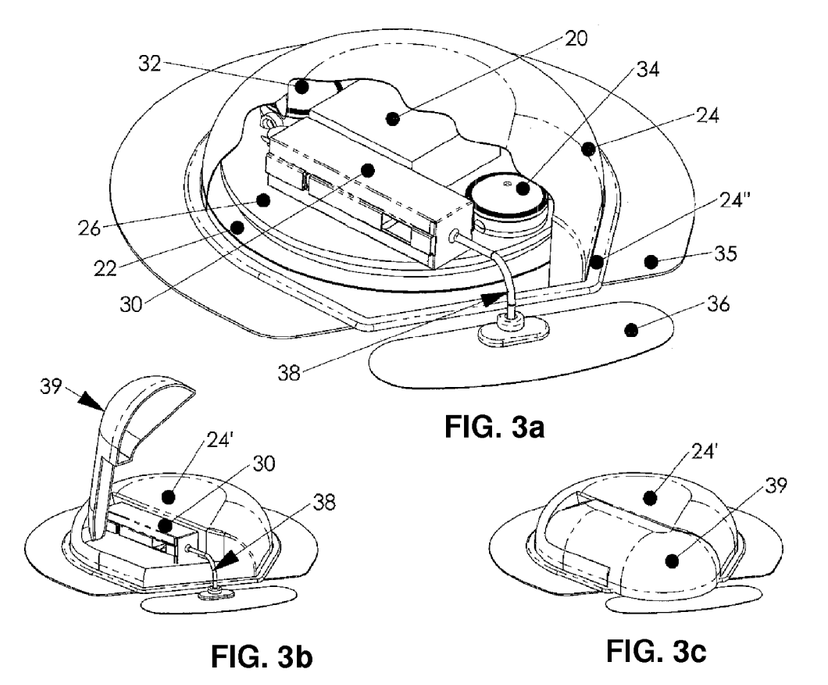
FIGS. 3a to 3c are isometric views showing details of an embodiment of the drug-delivery device of the present invention.

FIG. 3a shows a cut-away view of an embodiment of the drug-delivery device having a cannula insertion mechanism 30 that together with an associated cannula 28 (shown in FIG. 3d) serves as a drug administration device. As before, the battery cell is located between the cover part of the housing 24' and the pouch assembly 22. As the housing 24 is relatively flat in order to be as "patch-like" as possible, and as the diameter of battery cell 20 is smaller than the diameter of the drug pouch 22, the optimal location for at least part of the insertion mechanism 30 is above the drug pouch 22, and adjacent to the battery cell 20, in the free space available between the top of the housing 24' and the displaceable wall 26. Such an embodiment efficiently exploits this free space, thereby ensuring a lower profile than would otherwise be possible.

The insertion mechanism 30 (detailed below in FIG. 3d) is adapted to insert the cannula 28, which be a soft cannula, in a safe fashion to the patient's skin, the cannula being guided in a stainless steel chute 38 to the insertion site, upon an activation action. The insertion mechanism 30 is connected to the reservoir via a flexible tube and, in some embodiments, is accommodated in the drug-delivery device in a floating fashion so as to prevent motion of the pump from affecting the insertion site at the distal end of the chute 38. In some embodiments, the chute 38 leads to the patient's skin via a dedicated adhesive bandage 36, separated from the adhesive bandage of the device 35, such as to further minimize the effects of motions and forces from the pump on the insertion point. Also shown in this figure are an outlet valve 32 and a filling valve 34 to the drug reservoir, both of which are further described in relation to FIG. 4 below.

FIG. 3b is a non cut-away illustration of the view shown in FIG. 3a, illustrating the full cover of the housing 24' and showing the lever 39. As opposed to devices such as described in U.S. Pat. No. 6,960,192 in which the drug reservoir and the cannula insertion mechanism are enclosed within the same housing; in the present invention the cannula insertion mechanism 30 is substantially external to the housing 24 that houses the drug reservoir 22. One advantage of this location of the insertion device is the relatively higher floatation freedom that can be achieved by the insertion device, thereby reducing stresses between the housing and the cannula insertion point. Another advantage of this arrangement is that it makes it simpler to maintain the device waterproof within the housing, as only the fluid connection (not shown) between the drug reservoir 22 and the insertion mechanism 30 needs to pass through the housing wall. By lifting the lever 39, the insertion device is armed and the activation button (not shown) is exposed.

FIG. 3c demonstrates the device after the insertion has been completed and the lever 39 is replaced to the lower position where it provides protection to both the insertion mechanism 30 and the insertion point. In some embodiments, the control panel is also located under the lever 39. In some embodiments the replacement of the level 39 to the lower position activates the insertion device.

Figure 3D:
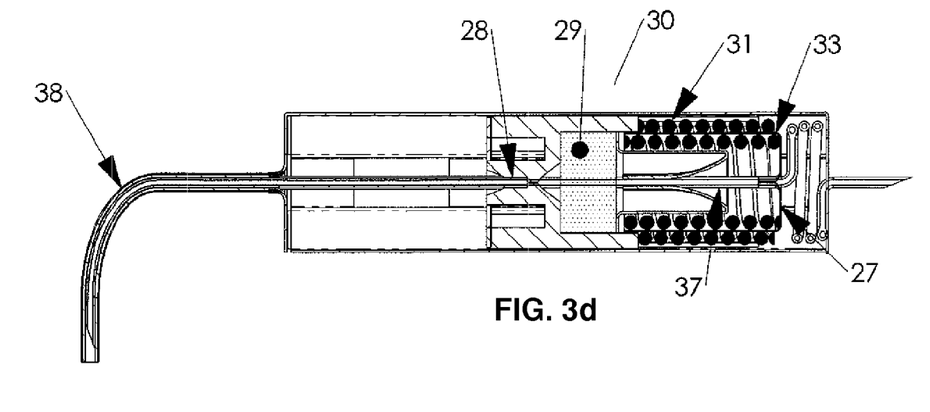
FIG. 3d is a cross-sectional view of the cannula insertion device.

FIG. 3d is a cross-sectional view of an embodiment of the needle insertion mechanism 30 shown in its pre-activation position. The device comprises a first biasing spring 31 for advancing the cannula 28 into the skin, a second biasing spring 33 for retracting a guiding needle set in the cannula 28 during the insertion, and an arrangement for activating the retraction action upon the completion of the penetration action of the cannula 28. The fluid to be delivered enters the insertion device 30 via the stainless steel tube 37 shown starting to the right of the figure, where the tube proceeds through the insertion device following a coiled path. The tube 37 continues through the mechanism 30 and through the cannula 28, and has a sharpened distal end extending from the distal end of the cannula, for facilitating the penetration of the cannula into the skin of the patient. The coiled section of the tube is designed as a compensation mechanism which allows the distal tip of the tube to advance with the cannula during the insertion action, while maintaining the proximal end of the cannula fixed. In the pre-activation position and during the insertion action, the distal end of the tube is attached to the cannula assembly via a spring cap 27 which is anchored to the cannula assembly via a retainer element (not shown). The spring cap 27 confines the retraction biasing spring 33 in a loaded position as long as the retainer element engages the spring cap 27 to the cannula assembly. The insertion biasing spring 31 forces the cannula assembly to the inserted position (leftward) together with the retraction biasing spring 33 (in the loaded state) and the spring cap 27. When the cannula 28 reaches its penetration end-position, the retainer element releases the spring cap 27 which disengages from the cannula assembly, allowing the retraction spring 33 to move it backward to the left, such that the tube's distal end is retracted into the cannula and away from the body. Thus a fully automated insertion procedure is carried by a single activation action. The cannula assembly further comprises a septum 29 which seals between the stainless steel tube 37 and the cannula 28, such that fluid entering the proximal end of the stainless steel tube 37 from the reservoir is constrained to exit from the distal end of the cannula 28 and therefore penetrate into the body. The activation is performed by operating a button or a lever (not shown) which releases the cannula assembly to move forward (leftward) and perform the insertion action.

It will be understood that the compensation mechanism presented in this embodiment can be replaced by other compensation mechanisms known in the art, such as a bellows coupler, a septum arrangement etc. It will also be understood that the septum seal between the stainless steel tube and the cannula can be replaced by alternative sealing solutions such as a bellows firmly connected to the stainless steel tube on one end and to the cannula at the other end. In other embodiment, the biasing springs are replaced by alternative biasing mechanisms known in the art. In some embodiments the retraction biasing spring is eliminated and the compensation mechanism's coils deliver the force for retracting the needle. In a further embodiment the proximal (receiving) end of the stainless steel tube terminates with a sharp end which is aligned with a septum leading to the reservoir, such that the fluid connection between the reservoir outlet path and the insertion device can be performed at a desired step of the assembly or during the treatment preparation procedure. In some embodiments the proximal end of the stainless steel tube is in permanent fluid connection with the outlet fluid path of the reservoir. In some embodiments, at least one of the biasing springs (31, 33) is loaded by the action of the lever 39, so as to avoid the mechanical stress and risk of early activation involved in having said spring(s) pre-loaded during storage.

FIGS. 4a to 4d show a further preferred embodiment 40 of the present invention, including a filling port and a generic outlet tube 45 for connecting to an administration device such as an IV infusion set.

Figure 4A:
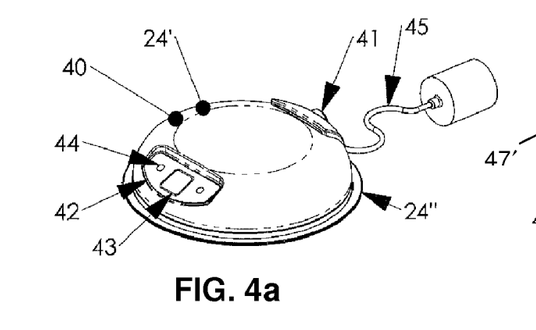
FIGS. 4a and 4b are isometric views showing use of a strain gauge within the drug-delivery device.

FIG. 4a is an isometric view of the assembled pump 40, showing a filling port 41 implemented in the housing 24 and an outlet tube 45 comprising a connector fitting at its distal end, which is typically a Luer-Lock connector. In other embodiments the distal end of the outlet tube 45 is directly connected to the administration device. This embodiment is an alternative to that presented above in connection with FIG. 3 in which the administration device is partly or mostly implemented within the device 40, enabling the outlet tube 45 to be eliminated. In a further embodiment the device 40 comprises a pre-filled reservoir and in this case the filling port 41 is eliminated. In a still further embodiment the reservoir is partly pre-filled with a pharmaceutical ingredient (or set of pharmaceutical ingredients) and the filling port 41 serves to fill the reciprocal pharmaceutical ingredient(s) to reconstitute the pharmaceutical product. In some embodiments the pre-filled ingredient is in the form of dry powder and the reciprocal ingredient is a reconstitution solution. Also shown in FIG. 4a is a control panel 42 (or HMI—Human Machine Interface) accommodated in a recess in the housing 24 such that the dome button 43 of the switch is mostly protected from accidental activation. The control panel 42 comprises a flat adhesive panel such that it provides a watertight seal to the reciprocal opening in the housing 24. Two light indicators 44 are provided, one on each side of the button 43. In some embodiments the switch 43 is protected by a door (not shown) in order to prevent accidental activation. The door can be transparent or semi-transparent to enable visualization of the light indicators. In some embodiments the transparent door comprises an optical device such as a lens in order to optimize the desired light effect. Other features that can be implemented in the HMI include a buzzer, a graphic display, and a communication port.

Figure 4B:
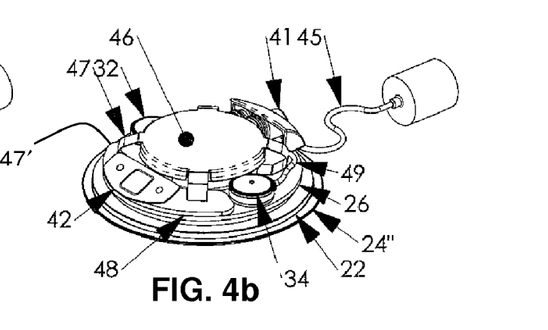

FIG. 4b shows the same embodiment as shown in FIG. 4a (in the same orientation) but having the upper part of the housing 24' removed in order to display the internal arrangement. The control panel 42 is located in proximity to a printed circuit board 48, to which it is wired. The outlet valve 32 and the filling valve 34 are shown, as is the conduit 49 connecting the filling port 41 to the filling valve 34. In some embodiments the valves are incorporated into the interfacing plate 26, adjacent to its perimeter, thus making efficient use of the free space surrounding the relatively small footprint battery cell 20 and the relatively large diameter reservoir pouch 22. The drug-delivery device may further comprise a pressure sensor which may be implemented within the reservoir 22 or anywhere in the fluid path between the reservoir and the administration device, or even placed externally to the flexible pouch or attached thereto. For example, it may be printed on the outer surface of the pouch thus obviating the need to test for sterility of the pressure sensor. An example of such a pressure sensor is a force sensing resistor as provided by Sytek Enterprises, Inc. of British Columbia, Canada.

The functions of the control module (42 and 48) may include any of the following: (a) detecting occlusion via the pressure sensor, in which case the drug delivery is halted; (b) controlling the drug-delivery rate, for example by loading of a resistance across the poles of the battery cell in order to drive the expansion of the battery cell, (c) detecting that the button has been depressed in order to provide a greater discharge rate across the battery poles and therefore deliver a bolus of drug, (d) implement a "lock-out" between boluses, (e) determine the basal and bolus rates, and detect device malfunctions, (f) store a history of the drug delivery, and (g) provide external communications, for example to an external remote controller or telephone equipped with Bluetooth.

In some embodiments the drug-delivery device further incorporates a displacement measuring device which measures the actual displacement of the battery cell or reservoir, in order to provide an indication of the volume delivered. This function may be provided by the use of a strain gauge. In some embodiments, the strain gauge is implemented in conjunction with a biasing plate 46 placed above the battery cell 20 as described below. The biasing plate 46 comprises a mostly central flat section which leans against the battery cell 20 from above and is held by a number of peripheral clips 47 which are anchored to the interface plate 26. At least one of the clips 47 incorporates a strain gauge 47' or an alternative strain probe that provides information on the distance between the biasing plate 46 and the interfacing plate 26, thereby providing information on the expansion of the battery cell 20 and enabling a closed loop control of the actuation.

The biasing plate 46 may be fabricated from stainless steel or from a bi-metal strip. In some embodiments the straingauge or the alternative strain probes, as well as the conductive paths leading to them, are implemented in the biasing plate 46. In some embodiments at least part of the biasing plate is a printed circuit board, which may be a "flex" type PCB with which the lateral clips 47 may be integral. In some embodiments at least one lateral clip 47 of the biasing plate 46 is connected to a main printed circuit board 48, thereby effecting the electrical connection between the PCB 48 and the strain probes. In some embodiments the biasing plate 46 applies to the battery cell 20 an initial force load constituting an opposing force to that of the battery's expansion (or the reservoir's depletion) as described above. In some embodiments the biasing plate 46 at least partially extends around the battery cell 20, thereby comprising a subassembly ready for insertion into the device housing 24. In a further embodiment the biasing plate or at least part of the functions of the biasing plate 26 listed above may be implemented in the wall of the battery-cell 20. The distal ends of the lateral clips 47 are firmly connected to the interfacing plate 26 or the circuit board 48 by means known in the art including adhesive layer, applied adhesive, electric or data connector, soldering, or any other suitable mechanical interface.

Although the position measurement is described here in relation to the battery expansion, it will be understood that the position measurement is equally indicative of the reservoir 22 contraction.

In some embodiments a multiplicity of strain probes or other position sensors can provide redundant information which enhances the measuring reliability. The redundant measurement can be analyzed to monitor the extent to which the interface plate is advancing in a parallel manner and its implications on the delivered fluid, as well as detecting any malfunction in the battery cell 20 expansion. The expansion of different sections of the battery cell 20 can be separately controlled. If the device 40 comprises a plurality of battery cells 20, a plurality of expansion probes can support the selective control of the motion of the interfacing plate 26.

Figure 4C:
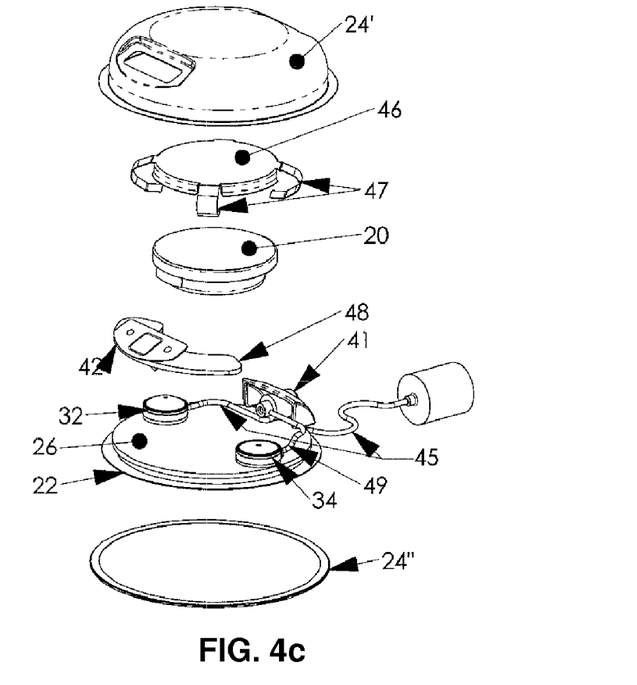
FIGS. 4c and 4d show respectively an exploded view and a cross-sectional view of the device shown in FIGS. 4a and 4b.

FIG. 4c is an exploded view of the device 40 showing further details thereof. In particular, the fluid conduit from the reservoir 22 to the outlet tube 45 is clearly seen as it routes from the outlet valve 32 in the interfacing plate, under the filling port, and through to the connector fitting.

Figure 4D:
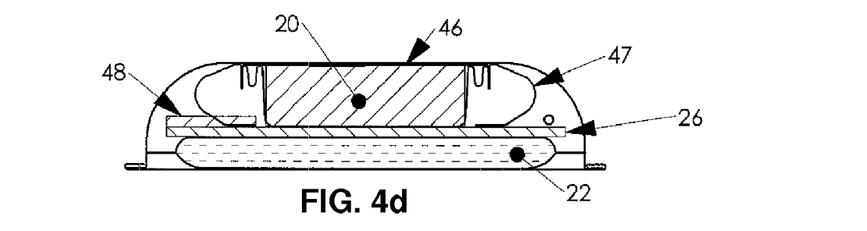

FIG. 4d is a cross-sectional view of the device 40, showing the relationship between the biasing plate 46 and the interfacing plate 26. In this embodiment, one of the lateral clips 47 is connected directly to the interfacing plate 26 while the other lateral clip 47 is connected to the PCB 48 which in return is firmly attached to the interfacing plate 26. For expansion probes positioned on both clips 47 it may be beneficial to route the conductive paths of all the expansion probes to the clip 47 that is connected to the PCB 48. A particularly effective position for the probe on each clip is on the sharp bend section at about the middle of the clip. The interfacing plate 26 may serve as a part of the displacement measuring device where a capacitance-based mechanism is used to determine the actual displacement achieved. In this case, the capacitance between the interfacing plate 26 and the base plate 24" of the housing 24 is measured using circuitry as described in connection with FIG. 9 below.

Advantageously, such strain gauges can also be very inexpensive (of the order of a few US cents at high volumes) and thus the addition of such a gauge does not add significant cost to the device, but does provide an important safety feature. An example strain gauge is the disposable EP-08-015DJ-120 model from Vishay Micro-Measurements, Inc. (Raleigh, N.C., USA). This gauge provides 0.3% accuracy over a resistance close to 120 ohm, and thus constitutes a useful and cost-effective means of providing the required displacement information. The displacement may alternatively be measured using other methods known in the art including, piezoelectric sensors, magnetostrictive sensors, active or passive optical sensors, capacitance sensors, and magnetic sensors, etc.

Figure 5:
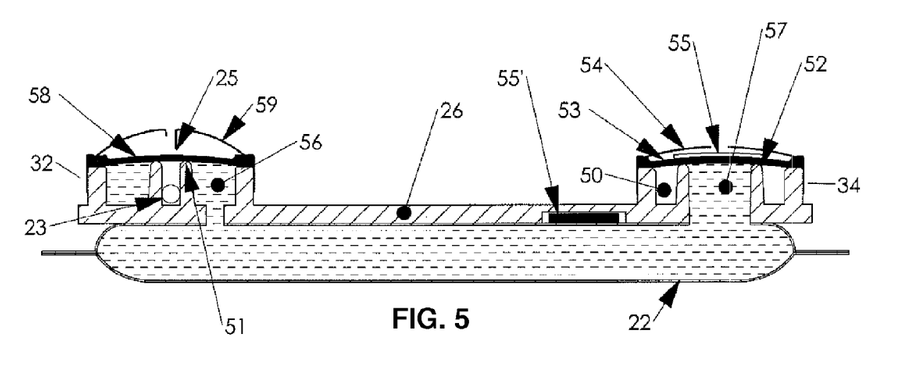
FIG. 5 is a cross-sectional view of an embodiment of a pouch-style reservoir for incorporation into the device of the present invention.

FIG. 5 is a cross-sectional view of the reservoir assembly of the device shown in FIG. 4. The interfacing plate 26 is firmly connected to the wall of the pouch leaving fluid-tight sealed ports between the reservoir 22 and the valves 32 and 34. The primary purpose of the outlet valve 32 is to avoid spillage or uncontrolled exit of drug from the reservoir 22 to the drug administration means while, in the particular embodiment shown, the outlet valve 32 also comprises a safety feature for exhausting excess pressure in case of over-pressure in the pouch (in the case of a malfunction of the device 40). The primary purpose of the inlet valve 34 is to allow filling of the pouch reservoir 22 while maintaining the integrity of a sealed reservoir thereafter. In order to achieve this purpose, a simple check valve would be sufficient, but in this particular embodiment the filling valve 34 has a secondary purpose: that of a redundant exhaust valve to assist in preventing excess pressure in the reservoir 22. Accordingly, in this embodiment, the valve is designed differently from a simple check valve. Specifically, the filling valve 34 comprises a peripheral annular wall and an internal annular wall which terminates with a sealing lip 52. An annular cavity 50 is defined between the peripheral wall and the inner wall which is in fluid connection with the filling tube (not shown) which connects to the filling port 41 (shown in FIG. 4*c*). A diaphragm 53 rests on the peripheral wall and is permanently sealed to it by a fluid-tight seal due to a press fit of the cover 54. The geometries and mechanical properties of the filling valve 34 and the diaphragm 53 are such that a predefined force is present between the sealing lips 52 and the diaphragm 53 to form a preset fluid-tight seal under a given threshold pressure. When the pressure in the filling line rises, the diaphragm 53 is forced away from the sealing lips 52 by the pressure built up in the annular cavity 50, thereby allowing the passage of the fluid from the filling line to the reservoir 22. In the filling process it is desired to hold the device 40 in a particular orientation such that most of the air content in the reservoir 22 will evacuate through the outlet valve 32. It is desirable to continue the filling process until the entire outlet passage and the administration device are free of air bubbles. Upon completion of the filling process, the pressure in the filling line drops, allowing the diaphragm 53 to return to its preset sealing position. In the event that hazardous excess pressure is built up in the reservoir 22 (for example due to a failure of the pressure sensor(s), or the control system, or within the battery cell, etc.), the pressure in the cavity 57 confined by the sealing lips 52 will force the diaphragm 53 to be displaced away from the sealing lips 52. This will release the excess pressure from the reservoir 22, thereby reducing the risk of a rapid unwanted discharge (i.e. bolus) from the reservoir to the body.

A pressure sensor 55 may be incorporated in the diaphragm 53 and wired to the control circuitry so as to provide actual pressure values in the reservoir to further enhance the control system and to provide early warning of occlusion or feedback regarding an empty or unsealed reservoir. Alternatively, the pressure sensor 55' may be accommodated in a recess in the interfacing plate 26.

The outlet valve 32 comprises a peripheral annular wall and an internal annular wall which terminates with a sealing lip 51. A diaphragm 58 is attached to the peripheral wall and is permanently fluid-tight sealed to it via a press fit of the cover 59. The geometries and mechanical properties of the valve 32 and the diaphragm 58 are such that a predefined force present between the sealing lip 51 and the diaphragm 57 forms a preset fluid-tight seal below a given threshold pressure. When the pressure in the reservoir 22 rises, the diaphragm 58 is forced away from the sealing lip 51 by the pressure built up in the annular cavity 56 defined between the peripheral wall and the inner wall, and upon a predefined threshold pressure the diaphragm 58 will be displaced away from the sealing lips 51 to allow the release of the excess pressure to the outlet cavity 23 which is in fluid contact with the outlet passage and thereby to the drug administration device. Thereafter, the diaphragm 58 returns to the preset sealing position. If hazardous excess pressure is built up in the reservoir (which in this case indicates failure of the pressure sensor(s), or the control system, or the battery cell; together with a failure of the exhaust feature of the filling valve 34), the diaphragm 57 will be displaced further until it meets the sharp point 25 of the valve cover 59 and is ruptured thereby, thus releasing the excess pressure from the reservoir, and preventing potential instant discharge of an undesired bolus from the reservoir 22 to the patient's body. It is advantageous to have a relatively large diaphragm surface in both the filling valve 34 and the outlet valve 32. This allows for better pressure sensitivity, higher sealing forces and smaller effects of mechanical "noises" or hysteresis effects. Additionally, the space between the relatively small footprint of the battery cell 20 and the relatively large diameter of the interfacing plate 26 provides an excellent location to accommodate these large valves. In one embodiment the interfacing plate 26 and the valve housing are made as a single unit, preferably molded from polyacetal, polyester, polycarbonate or PVC. It will be understood that the valves presented in this embodiment can be replaced with an alternative valve arrangement, including the use of off-the-shelf standard valves.

In some embodiments the valves 32 and 34 are separate units assembled to the relatively flat interfacing plate 26. The interfacing place 26 may be fabricated from a printed circuit board upon which at least some of the electronic components and circuitry are directly implemented. A pressure sensor may be directly implemented on the PCB facing the pouch wall. A micro-fluidic device may be implemented in the PCB or in components implemented thereon. Such a micro-fluidic device may be a flow sensor for measuring the flow rate from the reservoir to the patient's body or a valve. The PCB may comprise a temperature sensor facing the pouch's wall. In some embodiments the pressure sensor is located on the outlet line after the outlet valve, such that the sensed pressures more closely represent the pressure at the insertion site, thereby providing more accurate information on the delivery conditions and earlier occlusion detection.

The low-profile drug-delivery device of the present invention is not limited to the thin-film battery as described above. As noted above, the expansion of such batteries is limited to a range of about 40-60% relative to their initial thickness. In order to utilize the intercalation effect to attain a greater relative expansion, a different battery cell design is used, which employs the intercalation effect together with a hydraulic amplification within the battery cell, to produce a cell in which the initial thickness is less than that of those described above, but where the displacement produced can be similar or greater.

FIGS. 6*a* to 6*g* show one embodiment of such a cell 60, where the intercalation causes the electrolyte to serve as a hydraulic fluid which maximizes the displacement achieved on the interfacing plate 26.

Figure 6A:
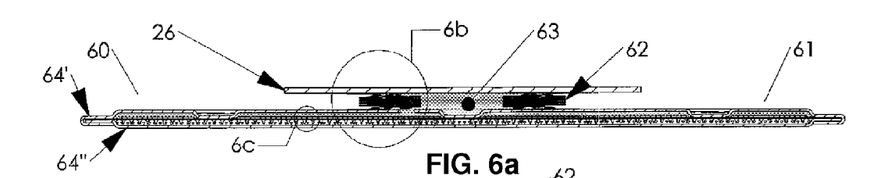
FIGS. 6a to 6f are cross-sectional views of an embodiment of the battery cell employing internal hydraulic amplification of the volume change resulting from the intercalation.

FIG. 6*a* is a cross-sectional view of the expanding cell 60 at its initial stroke position; i.e. before depletion and expansion. The expanding cell comprises a relatively large diameter and low profile electro-chemical cell 61, in fluid connection with a bellows structure 62 which is attached to the interfacing plate 26. The interiors of both the bellows 62 and the electrochemical cell 61 are filled with hydraulic fluid 63 that constitutes the total volume of fluid in the expanding cell. The bellows 62 may be fabricated from a stack of bent annular plates, connected in a fluid-tight sealed fashion on their inner and outer diameter by welding, thereby enabling axial expansion as the hydraulic fluid is transferred from the electrochemical cell 61 into the bellows 62. The electrochemical cell is encapsulated in a substantially rigid shell 64' and 64" which is substantially not deformable under relevant pressures and forces, and therefore its volume remains mostly constant.

Figures 6B, 6C, 6D:
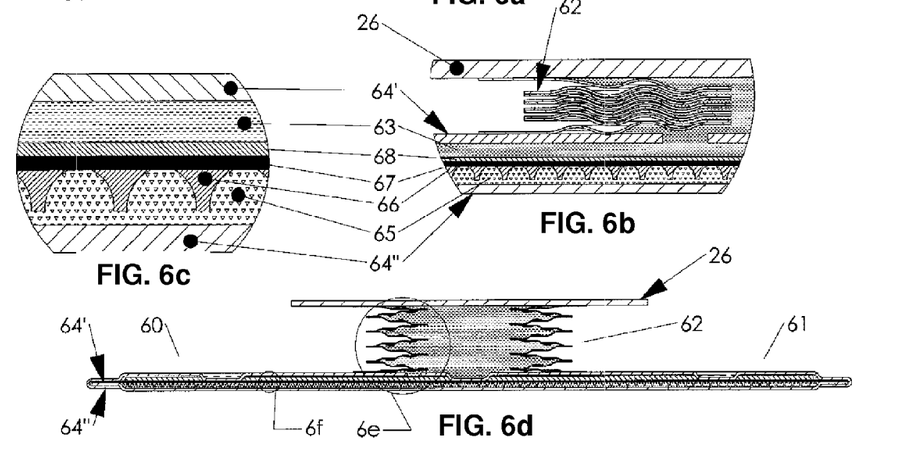

FIGS. 6*b* and 6*c* are enlarged detail views of the cell structure described above. On the inner side of the lower shell case 64" a composite layer is formed comprising a matrix material 65 (or accumulating matrix) which is chemically inert (to the relevant environment) and is electrically-conductive, and the intercalation material 66. The composite layer defines a first electrode which is in electrical contact with the shell case 64". The composite layer (65 and 66) is covered with a solid and substantially rigid electrolyte layer 67, on top of which there is disposed a second electrode 68 that is in electrical contact with the upper part of the shell case 64'. The remaining space between the second electrode 68 and the upper shell case 64' is filled with the hydraulic fluid 63. The lower shell case 64" and the upper shell case 64' are electrically isolated from each other by an intermediate seal (not shown). Upon closing an electric circuit between the first shell 64" and the second shell 64' the intercalating substance 66 migrates from the composite layer (65 and 66) through the electrolyte/membrane 67 to the second electrode 68 causing the second electrode 68 to expand, thereby forcing the hydraulic fluid 63 out of the electrochemical cell 61 and into the bellows 62. The transportation of the hydraulic fluid 63 into the bellows 62 causes the bellows to expand and move the interfacing plate 26. The arrangement of the composite layer is such that upon the depletion of the intercalating material 66 from the composite layer, the solid electrolyte/membrane 67 does not collapse into the emptying volume. The space of the migrated intercalation substance in the composite layer (65 and 66) may be at least partially replaced by a liquid electrolyte.

The accumulating matrix 65 may be a mesh, grid, sintered material, MIM, or any other porous material that can be impregnated (or otherwise filled) with the intercalating substance such that the accumulating substance maintains a continuous and mostly flat support between the first shell case 64" and the solid electrolyte 67. The sintering described above can be performed directly on the shell case 64" and may be performed with the intercalation material already mixed with the accumulating material. In some embodiments, the accumulating matrix 65 may be directly formed in the inner wall of the shell case 64" by means of notches and/or ridges formed in the surface by punching, laser cutting, machining etc. Another method of forming the accumulating matrix is by thin-layer construction methods as known in the art including spattering, electric deposition, chemical deposition, evaporation etc. The matrix layer 65 can be built prior to filling the intercalating material or the two can be built simultaneously. The solid electrolyte and/or the second electrode 68 may be formed by thin-layer construction methods including those listed above. In some embodiments the intercalating substance 66 contains Li, the second electrode contains Tin (Sn), and the solid electrode/membrane 67 is made of Lithium Phosphorus Oxynitride—commercially known as LiPon.

The bellows can be fabricated by a number of methods including thin metal layer deposition on lost-core. Alternatively, the bellows can be fabricated from plastic such as PVC or Polyester resins. The expanding wall may have a geometry that is different than a bellows. In either case, it will be understood that the bellows 62 or an alternative expanding shape does not have to be directly attached to the electrochemical cell 61 but instead the hydraulic fluid in the two units can communicated via a tube or the like. The hydraulic fluid 63 may be the electrolyte or may separate from the electrolyte.

Figures 6E, 6F:
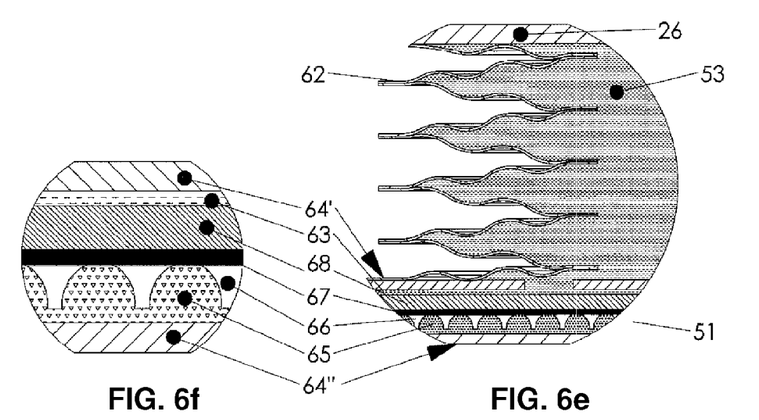

FIGS. 6d to 6f show the expanded position of the cell 60 where most of the intercalating material 66 has migrated into the second electrode 68 causing the electrode 68 to fully expand, thereby displacing the hydraulic fluid 63 into the bellows. As seen clearly in FIG. 6d, due to the hydraulic arrangement within the cell, the hydraulic fluid creates a major displacement despite starting from a very low profile, thereby providing a kind of hydraulic amplification to the intercalation effect.

Figure 6G:
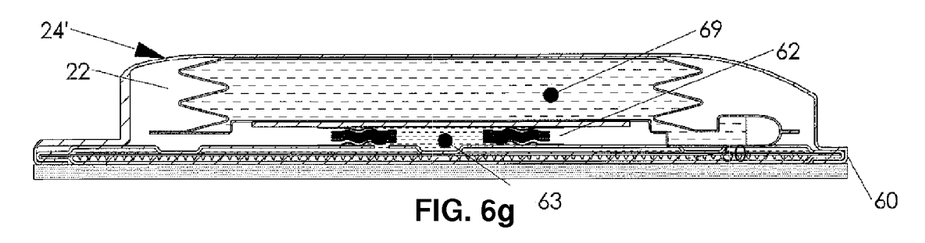
FIG. 6g is a cross-sectional view showing integration of the cell into the drug-delivery device.

FIG. 6g is a cross-sectional view showing a battery cell based on intercalation and using this hydraulic approach integrated into the drug-delivery device of the present invention. This approach enables a very low-profile construction, where the capacity of the cell (and therefore its volumetric expansion) is increased by spreading the battery laterally. The accumulated volumetric expansion is translated to a linear displacement by a hydraulic transformation as detailed above. The relatively thin and wide diameter of the battery cell make it preferable to locate this design of battery in the device closer to the body of the patient, where a smaller-diameter reservoir is placed more distantly from the body, allowing for a smooth curvature of the device's cover shell 24' and therefore less interference with clothes or other objects while wearing the device on the body. The reservoir 22 of this embodiment is fabricated from relatively stiffer films (as compared to the softer material from which the flexible pouch is formed) and therefore constructed with a bellows profile which allows for an easy and pre-arranged collapse of the film structure. Nevertheless such a reservoir structure has a tendency to resist this collapse owing to the rigidity of the film. Advantageously, this provides stability and resistance to the battery expansion, both of which contribute towards mechanical noise reduction. As will be understood, it is also possible to use the battery cell as per FIGS. 6a to 6f above as a one-to-one replacement of the battery cell shown in FIG. 2. In this case, it should be noted that the orientation of the battery cell is reversed, and a pouch-style reservoir may be used as per FIG. 2.

The reservoir to be used in the drug-delivery device of the present invention needs to accord to the design goal of enabling a low-profile patch-like product to be implemented, where the expansion of the battery presses against this reservoir. Two types of reservoir meeting this requirement have been detailed above: a slim pouch-style reservoir, and a bellows type film reservoir. In a further embodiment, a low drum-style reservoir can be used, approximately in the shape of a Petri dish, where a broad piston enters the drum (or vice versa), preferably using an "O" ring for sealing between the two.

Figure 7:
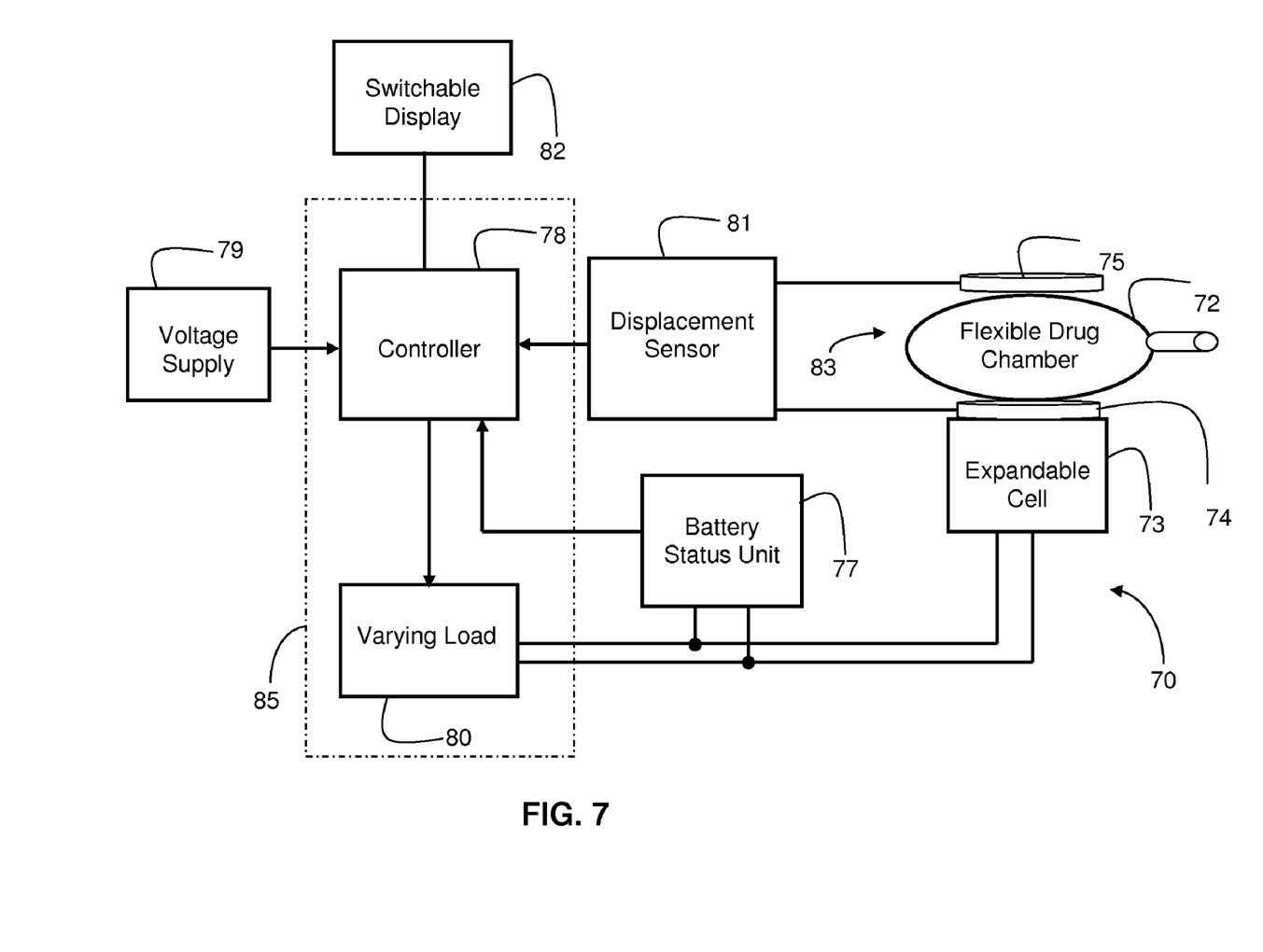
FIG. 7 is a block diagram showing the functionality of an electronic control system for controlling the rate of infusion in response to a measurement of actual displacement.

FIG. 7 is a block diagram showing functionally a control system 70 for controlling the rate of infusion in a drug-delivery device such as that described above with reference to FIGS. 1 to 6 of the drawings. The drug-delivery device may include a flexible chamber 72 serving as a drug reservoir on which pressure is exerted by an expandable cell 73 via a plate 74 disposed proximate a first side of the flexible chamber 72. A second plate 75 is disposed proximate a second, opposite side of the flexible chamber 72. One of the plates could be part of an outer casing of the device or coupled thereto as shown in FIG. 4d above.

The system 70 comprises a battery status unit 77 that is coupled to the cell 73 and measures one or more properties thereof that provides a measure of the discharge of the cell 73. Such properties may include, by way of example, temperature, voltage, battery current and internal resistance. Internal resistance of the cell can be determined by using a switching circuit, such as a MOSFET, to intermittently connect a resistive load across the cell and to measure the voltage both with and without the load connected. The internal resistance of the cell can be determined by dividing the difference in voltage levels without load and several microseconds later when the load is connected by the current when the load is applied.

The battery status unit 77 monitors the discharge of the cell 73 and provides a control signal to a controller 78 powered by a DC voltage supply 79. The controller 78 generates a control signal responsive to the measured discharge and feeds the control signal to a varying load 80 that is applied to the expandable cell 73 so as to vary its rate of discharge. The varying load 80 is a circuit whose output impedance varies as a function of the control signal so that as output impedance increases, the expandable cell 73 discharges more quickly and vice versa. A displacement sensor 81 is coupled to the two plates 74 and 75 for measuring the relative displacement of the plates 74 and 75 and provides a feedback signal indicative of the measured displacement to the controller 78. A switchable indicator 82 may be coupled to the controller 78 to provide a visible and/or audible indication of cell discharge, thus providing feedback of the rate of drug delivery. The controller 78 in conjunction with the varying load 80 operates as a constant current depletion circuit 85, of which specific implementations are described below with reference to FIGS. 8a and 8b of the drawings.

In such an arrangement, the controller 78 is responsive to actual discharge of the expandable cell 73 for varying its rate of discharge. In fact, even without the feedback loop provided by the displacement sensor 81, the controller provides accurate drug delivery response to a desired administration regime based on a predetermined relationship between (a) the discharge of the battery, (b) the resulting displacement of the interfacing plate and (c) the relationship between the displacement of the interfacing plate and the volumetric change of the reservoir. However, by also incorporating actual positional information provided by the displacement sensor 81, two indications of volumetric drug delivery can be attained— one based on battery cell depletion and one based on measured displacement. An algorithm combining both indications can serve to provide more accurate data concerning the actual drug delivery than either one alone. Additionally, by comparing these two indications, device malfunctions can be detected and the controller 78 can then act according to the program for such conditions, thereby adding a further safety feature to the device.

It will be understood that while in the above embodiment the controller is responsive to battery status and the measured displacement is used to provide additional feedback, it is also feasible to use measured displacement as the primary yardstick and optionally to use the feedback provided by monitored battery status as an additional safeguard. In either case, regardless of whether the controller relies solely on the measured property of the cell or on measured relative displacement of the plates or on both of these, it will nevertheless be understood that the controller 78 is indirectly responsive to displacement generated by the battery.

As noted above, the actual discharge is a function of the measured relative displacement of the plates 74 and 75. The displacement sensor 81 may, for example, be a strain gauge as described above with reference to FIG. 4. Alternatively, the plates 74 and 75 may be made of metal so as to form a parallel plate capacitor 83 of which the drug chamber serves as the dielectric and whose capacitance is a function of the spacing between the two plates 74 and 75 and thus varies as fluid content is exhausted from flexible chamber 72. In this case, the displacement sensor 81 may be a capacitance sensor for measuring the capacitance of the capacitor 83. Capacitance may be measured by applying a square wave current pulse to an integrator formed of an OP AMP across which the capacitor 83 is connected. The integrator outputs a sawtooth voltage whose slope depends on the capacitance of the capacitor 83. Slope can be measured using a threshold detector in known manner. The displacement can be estimated from the measured capacitance value or by the use of a lookup table containing experimentally determined data.

Figure 8A:
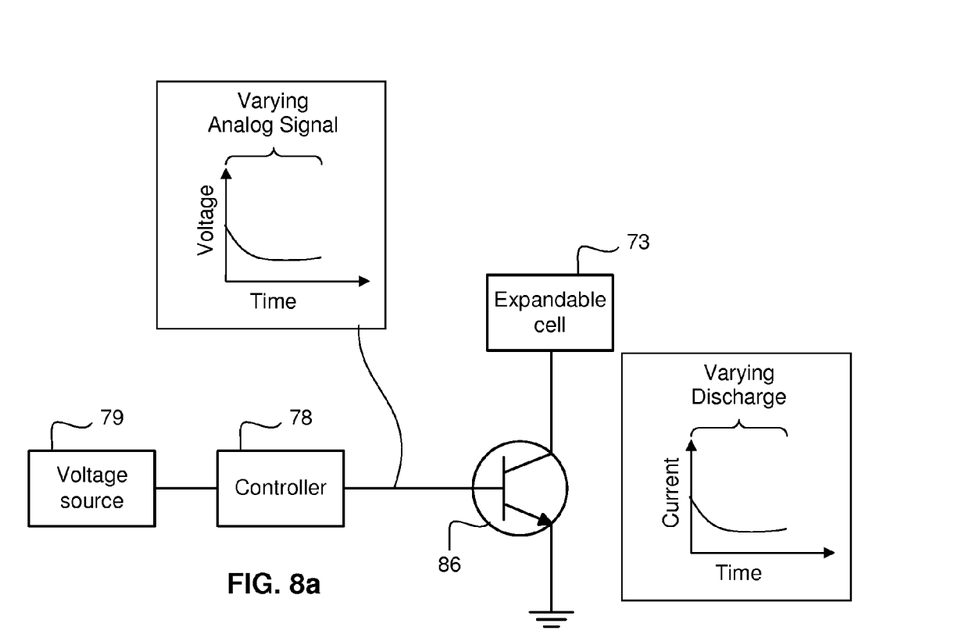
FIGS. 8a and 8b are electronic circuit diagrams showing circuits for generating a constant current depletion at a determined rate from the displacement-generating battery.

For any given infusion rate, the expandable cell 73 needs to be discharged at a constant current rate. As the internal resistance of the cell is subject to changes, a discharge circuit or current depletion circuit capable of providing constant current discharge is required. FIG. 8a shows one implementation of the current depletion circuit 85 where the varying load 80 is constituted by a bipolar junction transistor 86 to present a calculated resistance across the poles of the expandable cell 73 by applying a controlled bias voltage to its base terminal. Also shown is the current discharge characteristic of the cell, which is seen to follow the base voltage characteristic of the transistor 86.

Figure 8B:
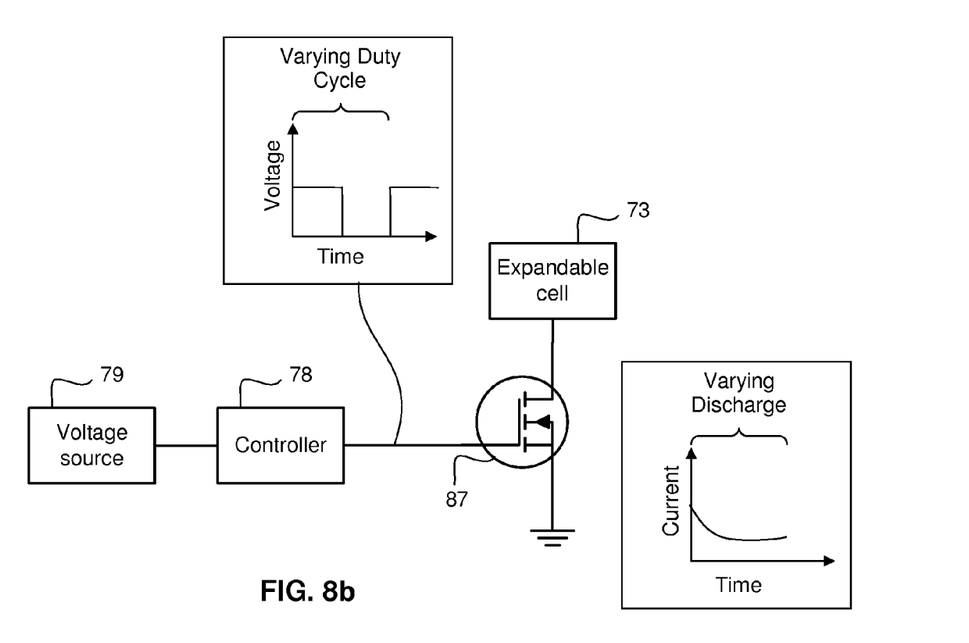

FIG. 8b shows an alternative implementation of the current depletion circuit 85 where the varying load 80 is constituted by a MOSFET 87 and pulse width modulation (PWM) is used to adjust the duty cycle of the MOSFET 87 (that operates as a PWM switch) so that the mean source-drain current varies. Thus, by varying the duty cycle of the MOSFET 87 the mean discharge current may be controlled.

The current-depletion circuit 85 may be settable to different depletion rates in order to generate different drug infusion rates, including but not limited to different basal rates and a range of bolus delivery rates. To this end, the controller varies the load in the current-depletion circuit 85 in response to a desired drug infusion rate. Thus, with reference to FIGS. 8a and 8b instead of only a single discharge characteristic being available there may be several, each relating to a respective drug infusion rate; and the controller adjusts the base bias voltage of the bipolar junction transistor 86 shown in FIG. 8a or the duty cycle of the MOSFET 87 shown in FIG. 8b so as to generate the appropriate discharge characteristic.

The drug administration device of the present invention may be an integral cannula or an external IV or subcutaneous device as described above. Alternatively, the administration device may include an intradermal or transdermal mechanism such as at least one microneedle or a microneedle array. In this case, due to the miniature nature of microneedle technology, a very small and flat product can be achieved. This is especially advantageous where the drug reservoir size is small, enabling a coin-like design to be implemented.

It should also be noted that while the use of hydraulic amplification has been described with particular reference to cells that use intercalation, it may also be used in conjunction with other displacement-generating batteries, including those using a different non-intercalation-based chemistry.

While the invention has been shown herein in what is presently conceived to be the most practical and preferred embodiment thereof, it will be apparent to those of ordinary skill in the art that many modifications may be made thereof within the scope of the invention, which scope is to be accorded the broadest interpretation so as to encompass all equivalent structures and devices.

What is claimed is:
1. A controllable drug delivery device for delivering a liquid injectable drug, said device comprising:
   a drug reservoir;
   a drug administration device;
   a displacement-generating battery;
   a displacement sensor for producing a signal indicative of the actual displacement produced by said battery;
   a current-depletion circuit;
   a controller for applying a variable load across said battery; and
   a battery status unit coupled to the battery for determining at least one property of said battery that is indicative of battery displacement;

wherein displacement generated by said battery under the control of said controller as current is depleted from the battery by the current depletion circuit displaces a wall of the drug reservoir thereby causing the reservoir to expel liquid injectable drug contained therein via said drug administration device, the inputs to said controller include both the displacement sensor and the battery status unit, such that two independent indications of the displacement achieved are available to said controller;

the controller is responsive to a discrepancy between said two indications for determining that a malfunction has occurred, and the controller provides a substantially constant-current depletion of the battery and thereby causes said drug delivery device to deliver a substantially constant drug delivery rate.

2. The drug delivery device of claim 1, wherein the properties of the battery determined by the battery status unit include internal resistance and accumulated discharge.

3. The drug delivery device of claim 1, where the drug delivery rate is calculated according to accumulated charge depletion from said battery.

4. The device according to claim 1, wherein the current depletion circuit is adapted to vary a duty cycle of a switch so as to vary a mean current passed thereby.

5. The device according to claim 1, wherein:

the current depletion circuit includes a bipolar junction transistor having a collector and emitter coupled across the battery, and the controller is adapted to apply a controlled bias voltage to a base of the bipolar junction transistor for varying an effective output impedance of the bipolar junction transistor.

6. The device according to claim 1, wherein the displacement sensor includes a strain gauge.

7. The device according to claim 1, wherein the displacement sensor is adapted to measure capacitance between a pair of electrically conductive plates disposed on opposite sides of the drug reservoir.

8. The device according to claim 1, wherein the current-depletion circuit is settable between different depletion rates in order to generate different drug delivery rates.

9. The device according to claim 1, wherein the controller is adapted to set lock-outs between boluses.

10. The device according to claim 1, wherein the battery operates based on intercalation between two metals.

11. The device according to claim 1, wherein the battery contains an electrochemical cell that is fluidly coupled to a bellows having an expanding wall and, on expansion of the cell, fluid is forced out of the cell into the expanding wall thus causing the expanding wall to expand.

12. The device according to claim 11, wherein the fluid is a hydraulic fluid.

13. The device according to claim 11, wherein the fluid is electrolyte.

14. The device according to claim 1, wherein the battery is a thin-film battery.

15. The device according to claim 1, wherein the battery provides sufficient pressure to deliver drugs in viscosity range 20-200 centipoise.

16. The device according to claim 1, wherein the drug reservoir includes a flexible pouch.

17. The device according to claim 16, wherein the cannula insertion mechanism is at least partially mounted in parallel with the battery.

18. The device according to claim 1, wherein the drug administration device comprises a cannula and an associated insertion mechanism.

19. The device according to claim 1, wherein the drug administration device comprises at least one microneedle.

* * * * *